(12) United States Patent
Kobayashi et al.

(10) Patent No.: US 10,621,413 B2
(45) Date of Patent: Apr. 14, 2020

(54) ANALYSIS-RESULT BROWSING DEVICE

(71) Applicant: OLYMPUS CORPORATION, Hachioji-shi, Tokyo (JP)

(72) Inventors: Mina Kobayashi, Tokyo (JP); Ayumu Sakurai, Tokyo (JP); Toshiyuki Hattori, Tokyo (JP); Naohiro Ariga, Tokyo (JP); Shinichi Takimoto, Tokyo (JP); Taiji Mine, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 84 days.

(21) Appl. No.: 15/926,949

(22) Filed: Mar. 20, 2018

(65) Prior Publication Data

US 2018/0285623 A1    Oct. 4, 2018

(30) Foreign Application Priority Data

Mar. 28, 2017    (JP) .................................. 2017-062847

(51) Int. Cl.
*G06K 9/00*    (2006.01)
*G06T 7/00*    (2017.01)
(Continued)

(52) U.S. Cl.
CPC ......... *G06K 9/00134* (2013.01); *C12M 41/36* (2013.01); *G01N 15/0205* (2013.01); *G01N 15/0612* (2013.01); *G01N 15/1463* (2013.01); *G06T 7/0012* (2013.01); *G06T 11/206* (2013.01); *G01N 2015/1006* (2013.01); *G01N 2015/1486* (2013.01); *G01N 2015/1493* (2013.01); *G01N 2015/1497* (2013.01); *G06T 2207/30024* (2013.01)

(58) Field of Classification Search
None
See application file for complete search history.

(56) References Cited

U.S. PATENT DOCUMENTS 6,329,139 B1 * 12/2001 Nova .................... B01J 19/0046
209/597
2003/0161515 A1 * 8/2003 Salmon .................. G02B 21/24
382/128

(Continued)

FOREIGN PATENT DOCUMENTS

JP    2005234435 A    9/2005
JP    5740101 B2    6/2015

*Primary Examiner* — Nancy Bitar
(74) *Attorney, Agent, or Firm* — Holtz, Holtz & Volek PC

(57) ABSTRACT

The number of cells existing and the positions thereof in a container that contains the cells can be grasped at a glance. Provided is an analysis-result browsing device that includes: a camera that captures cells at set capturing positions; a processing unit that detects and analyzes the cells captured by the camera, for the respective capturing positions; a display unit that displays analysis results of the cells analyzed by the processing unit, together with a container map that shows a container and the plurality of capturing positions in the container; and a control unit that sets the capturing positions in the container, which contains the cells, and simultaneously displays the analysis results of the cells at at least two of the capturing positions on the container map, which is displayed on the display unit.

6 Claims, 8 Drawing Sheets

(51) Int. Cl.
*G06T 11/20* (2006.01)
*G01N 15/06* (2006.01)
*G01N 15/14* (2006.01)
*C12M 1/34* (2006.01)
*G01N 15/02* (2006.01)
*G01N 15/10* (2006.01)

(56) References Cited

U.S. PATENT DOCUMENTS

| | | | |
|---|---|---|---|
| 2005/0051723 A1* | 3/2005 | Neagle | C12M 41/14 |
| | | | 250/306 |
| 2005/0082494 A1* | 4/2005 | Motomura | G02B 21/002 |
| | | | 250/458.1 |
| 2005/0234435 A1* | 10/2005 | Layer | A61B 17/3403 |
| | | | 606/1 |
| 2007/0064101 A1* | 3/2007 | Hasegawa | G02B 21/367 |
| | | | 348/79 |
| 2010/0158656 A1* | 6/2010 | Seavey | B25J 5/005 |
| | | | 414/744.5 |
| 2013/0013623 A1* | 1/2013 | Shah | G06F 16/284 |
| | | | 707/756 |

* cited by examiner

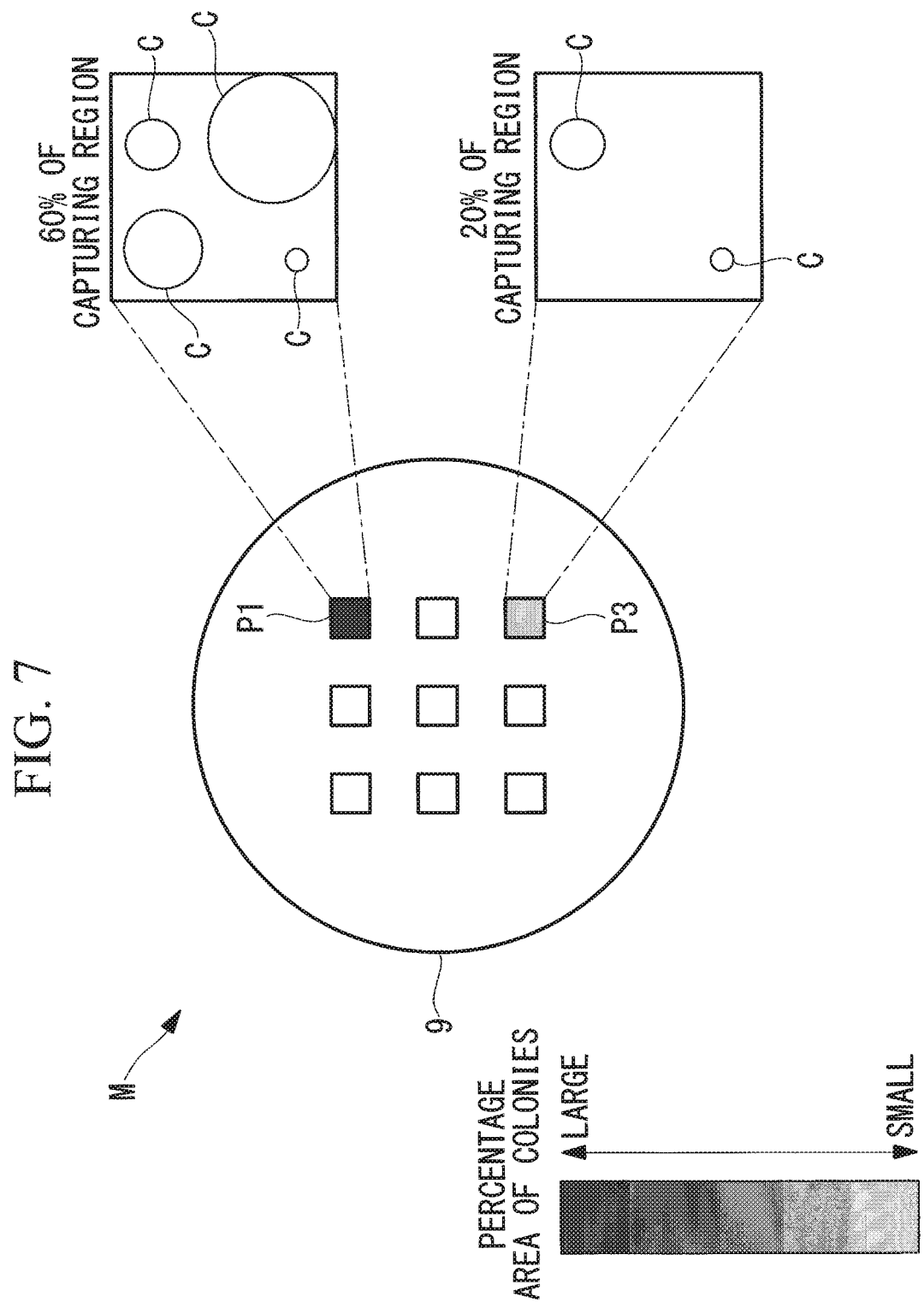

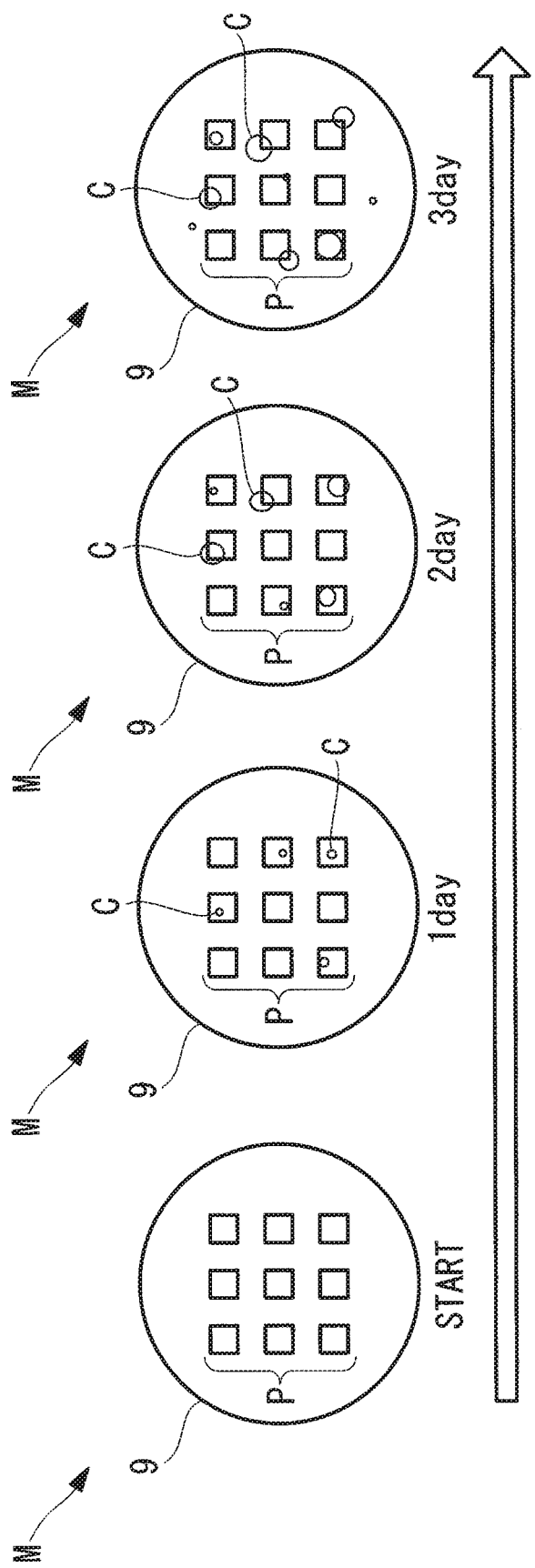

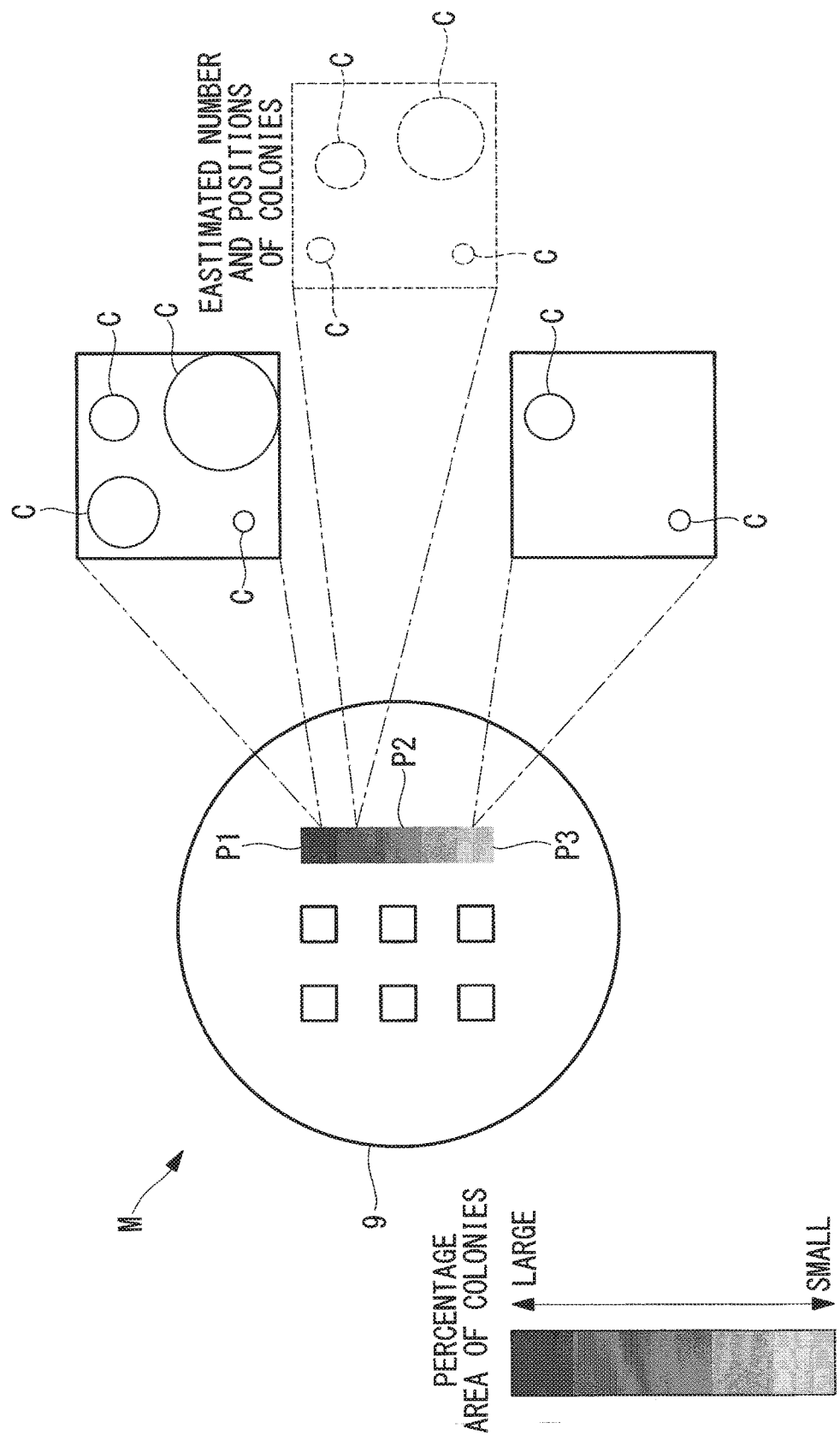

ANALYSIS-RESULT BROWSING DEVICE

CROSS-REFERENCE TO RELATED APPLICATIONS

This application is based on Japanese Patent Application No. 2017-062847, the contents of which are incorporated herein by reference.

TECHNICAL FIELD

The present invention relates to an analysis-result browsing device.

BACKGROUND ART

In the related art, there are known devices that measure the number of cells, the positions thereof, the sizes thereof, etc., by using an image acquired by capturing the states of the cells during cell culturing and that display changes in the states of the cells (for example, see PTLs 1 and 2).

In the technique described in PTL 1, the features of cells, such as the shapes, the sizes, or the like thereof, are extracted from an acquired image, the feature quantities thereof are calculated, and changes in the calculated feature quantities are reflected in setting culturing conditions. In the microscope observation device described in PTL 2, a microplate having a plurality of wells and a particular observation point for each of the wells are displayed on a monitor, and, when the user specifies the particular observation point, a luminance-value variation graph at the specified observation point is displayed superimposed on the microplate.

CITATION LIST

Patent Literature

{PTL 1} Publication of Japanese Patent No. 5740101
{PTL 2} Japanese Unexamined Patent Application, Publication No. 2005-234435

SUMMARY OF INVENTION

An object of the present invention is to provide an analysis-result browsing device making it possible to grasp, at a glance, how many cells exist at which positions in a container that contains the cells.

Solution to Problem

According to one aspect, the present invention provides an analysis-result browsing device including: a capturing-position setting unit that sets capturing positions in a container that contains cells; an image acquisition unit that captures the cells that exist at the capturing positions set by the capturing-position setting unit; an analysis unit that detects and analyzes, for the respective capturing positions, the cells captured by the image acquisition unit; a display unit that displays analysis results of the cells analyzed by the analysis unit, together with a container map that shows the container and the plurality of capturing positions in the container; and a display control unit that simultaneously displays the analysis results of the cells at at least two of the capturing positions on the container map, which is displayed on the display unit.

In the above-described aspect, the display control unit may display, at the capturing positions on the container map in a distinguishable manner, the outer periphery of a colony into which two or more of the cells detected by the analysis unit are aggregated.

In the above-described aspect, when the colony has a protruding region that partially protrudes from the corresponding capturing position, the display control unit may estimate the protruding region of the colony on the basis of the analysis results of the cells analyzed by the analysis unit and may display the estimated protruding region on the container map.

In the above-described aspect, the display control unit may calculate the feature quantity of a colony into which two or more of the cells are aggregated, on the basis of the analysis results of the cells analyzed by the analysis unit and may display the calculated feature quantity on the container map in association with the corresponding capturing position.

In the above-described aspect, the display control unit may display the feature quantities as 3D graphics, graphs, or color gradations, in a comparable manner at at least two of the capturing positions on the container map.

In the above-described aspect, the display control unit may estimate the feature quantity of a colony that exists in a region, other than the capturing positions, on the container map on the basis of the analysis results of the cells analyzed by the analysis unit and may display the estimated feature quantity of the colony on the container map.

BRIEF DESCRIPTION OF DRAWINGS

FIG. 7 is a plan view showing a state in which the feature quantities of colonies existing at the respective capturing positions are displayed in color gradation, as a modification of analysis results displayed at the respective capturing positions on the container map.

FIG. 8 is a plan view showing an example case in which changes obtained at capturing-time intervals are shown in a sequential manner like a moving image, as a modification of analysis results displayed at the respective capturing positions on the container map.

FIG. 9 is a plan view showing an example case in which estimated feature quantities of colonies existing in a region, other than the capturing positions, on the container map are displayed on the container map.

DESCRIPTION OF EMBODIMENT

An analysis-result browsing device according to one embodiment of the present invention will be described below with reference to the drawings.

Figure 1:
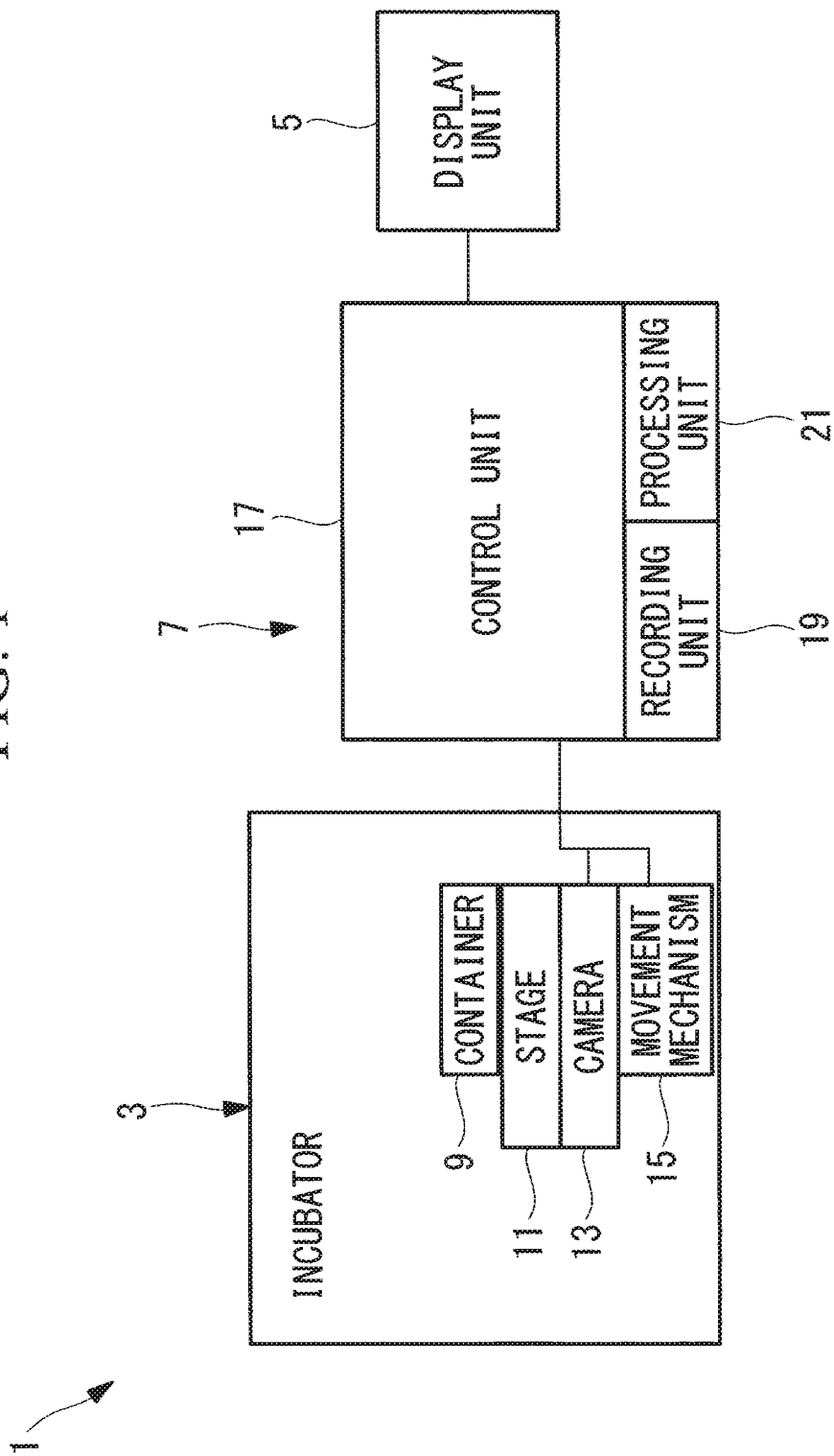
FIG. 1 is a view showing, in outline, the configuration of an analysis-result browsing device according to one embodiment of the present invention.

As shown in FIG. 1, an analysis-result browsing device 1 of this embodiment is provided with: an incubator 3 in which cells S (see FIG. 4) are cultured; a display unit 5 that displays an image etc. of the cells S cultured in the incubator 3; and a PC (Personal Computer) 7 that performs control of the incubator 3 and the display unit 5, recording of information, image processing, etc.

The incubator 3 is provided with: a stage 11 on which a container 9 that contains the cells S is mounted; a camera (image acquisition unit) 13 that captures the cells S in the container 9 mounted on the stage 11; and a movement mechanism 15 that moves the camera 13 in a direction intersecting the capturing optical axis thereof.

As the container 9, a petri dish, a flask, or the like for cell culturing can be used, for example.

Figure 2:
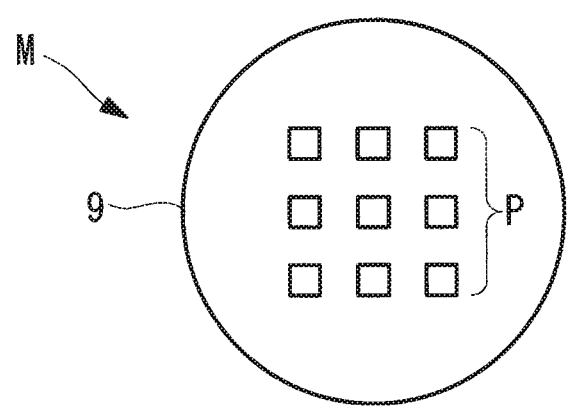
FIG. 2 is a plan view showing an example container map in the cases where a container is a petri dish.
Figure 3:
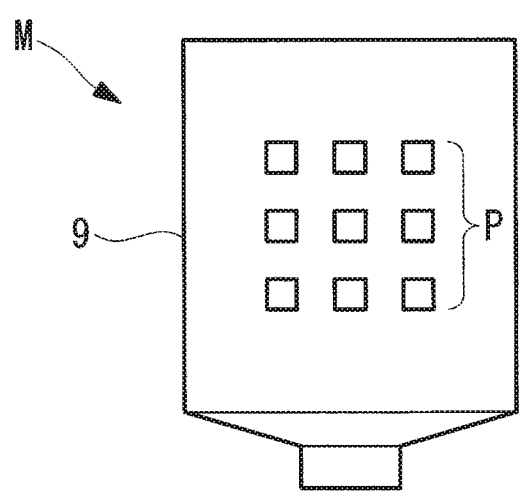
FIG. 3 is a plan view showing an example container map in the case where the container is a flask.

The display unit 5 displays an image of the cells S acquired by the camera 13 and displays a container map M, such as that shown in FIG. 2 or 3, that shows the container 9 and a plurality of capturing positions P in the container 9.

The container map M graphically shows the whole area of the container 9 and the plurality of capturing positions P in the container 9, in an associated manner with the actual sizes and positional relations. FIG. 2 shows an example container map M in the case in which the container 9 is a petri dish, and the number of capturing positions P is nine. FIG. 3 shows an example container map M in the case in which the container 9 is a flask, and the number of capturing positions P is nine.

The PC 7 is provided with: a control unit (capturing-position setting unit, display control unit) 17 that sets the capturing positions P in the container 9 and that controls capturing performed by the camera 13 and movement of the camera 13 performed by the movement mechanism 15; a recording unit 19 that records position information of the camera 13, images acquired by the camera 13, and the like; and a processing unit (analysis unit) 21 that processes the images recorded by the recording unit 19.

The processing unit 21 detects and analyzes cells S (or, colonies C into which cells S are aggregated, see FIG. 4) from images of the cells S acquired at the respective capturing positions P, the images being recorded by the recording unit 19, and causes the recording unit 19 to record analysis results indicating the sizes, the shapes, the locations, etc. of the detected cells S (or, colonies C) for the respective capturing positions P. The processing unit 21 detects, in the image, cells S that are equal to or larger than a predetermined size, for example, and excludes, from detection targets, cells S that are smaller than the predetermined size.

The control unit 17 can set the capturing positions P at a plurality of (in this embodiment, nine) locations in the container 9 with intervals therebetween. The control unit 17 drives the movement mechanism 15 and the camera 13, sequentially moves the camera 13 to each of the set capturing positions P, and causes the camera 13 to capture cells S at each of the capturing positions P. The position information of the camera 13 moved by the movement mechanism 15 and images of cells S at the respective capturing positions P acquired by the camera 13 are recorded by the recording unit 19.

The control unit 17 simultaneously displays the analysis results of the cells S processed by the processing unit 21, at the nine capturing positions P on the container map M displayed on the display unit 5. Specifically, the control unit 17 associates the external appearances of the cells S at the respective capturing positions P analyzed by the processing unit 21 with the actual sizes and positional relations and displays the external appearances of the cells S as simple graphics, e.g., circles and ellipses, simultaneously at all the capturing positions P on the container map M.

If there is a colony C into which a plurality of cells S detected by the processing unit 21 are aggregated, in a capturing position P, the control unit 17 surrounds the outer periphery of the colony C with a line and displays the colony C in a distinguishable manner from other regions, at the capturing position P on the container map M.

Figure 4:
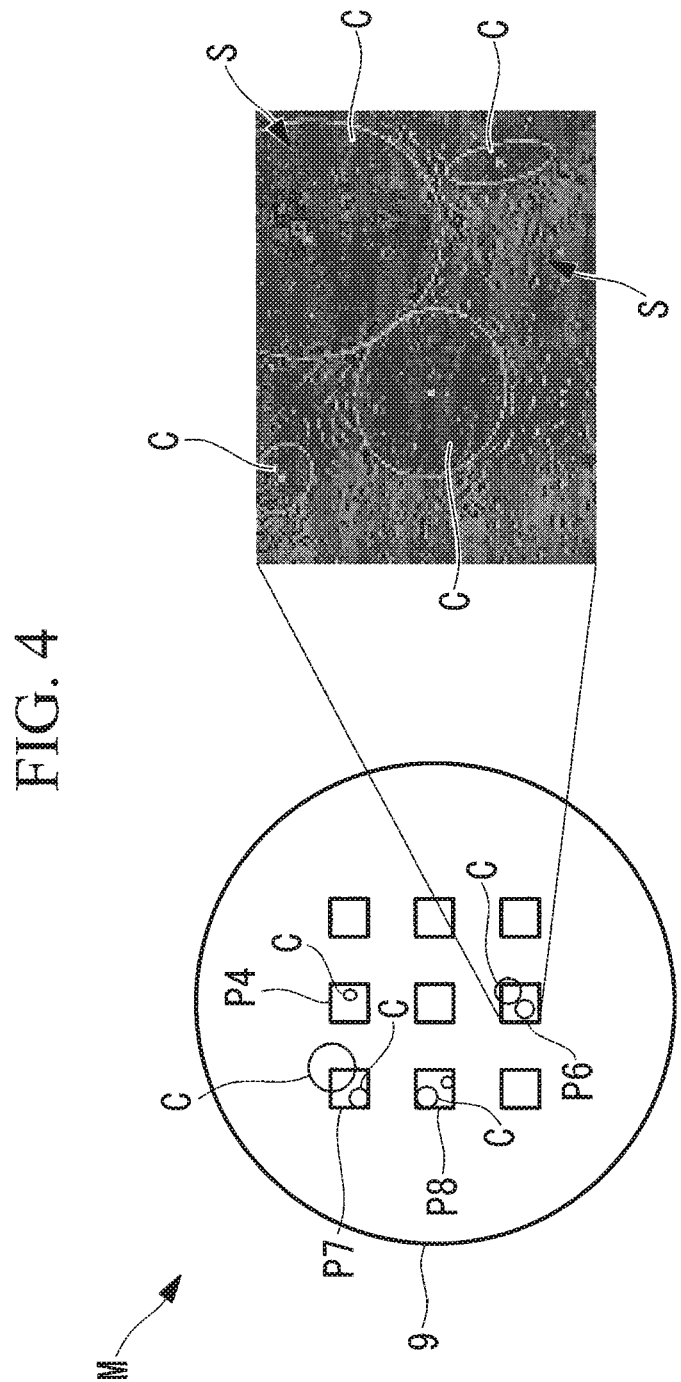
FIG. 4 is a plan view showing a state in which the external appearances of cells are simultaneously displayed as simple graphics at all capturing positions on the container map shown in FIG. 2.

If the colony C detected by the processing unit 21 has a protruding region that protrudes from the capturing position P, the control unit 17 calculates an estimate value for the protruding region of the colony C on the basis of the analysis result of the cells S analyzed by the processing unit 21. Then, the control unit 17 also displays, on the container map M, the outer periphery of the protruding region of the colony C beyond the region of the capturing position P, on the basis of the calculated estimate value, as shown in FIG. 4.

When the user specifies an arbitrary capturing position P on the container map M, the control unit 17 displays the state of that capturing position P in the container 9, in an enlarged manner. An item to be displayed in an enlarged manner may be an actual image acquired at that capturing position P, as shown in FIG. 4, for example, or only ROI (Region Of Interest) information indicating, with a line, the outer periphery of a colony C in that capturing position P, for example.

The operation of the thus-configured analysis-result browsing device 1 will now be described.

In order to observe cells S by using the analysis-result browsing device 1 of this embodiment, first, the user mounts the camera 13 and the movement mechanism 15 in the incubator 3, and a plurality of capturing positions P in the container 9 (in this embodiment, nine positions) are set by the control unit 17.

When cultured cells are to be captured, the whole region of the container 9 is not scanned, but some of the capturing positions P in the container 9 are captured, thereby making it possible to estimate the culture state of the cells S. Therefore, it is preferred that the plurality of capturing positions P be discretely set in the whole container 9. When the capturing positions P are set by the control unit 17, the container map M is displayed on the display unit 5.

Next, the control unit 17 drives the movement mechanism 15 and the camera 13 to sequentially move the camera 13 to the respective set capturing positions P, and the camera 13 captures the cells S at each of the capturing positions P. The position information of the camera 13 moved by the movement mechanism 15 and images of the cells S at the respective capturing positions P acquired by the camera 13 are respectively recorded by the recording unit 19 of the PC 7.

Next, from the images of the cells S at the respective capturing positions P recorded by the recording unit 19, cells S that are equal to or larger than the predetermined size are detected and analyzed by the processing unit 21 of the PC 7, and analysis results indicating the sizes, the shapes, and the locations, etc. of the detected cells S (or, colonies C) are recorded and accumulated by the recording unit 19 for each of the capturing positions P.

Next, the control unit 17 simultaneously displays the cells S (or, colonies C) analyzed by the processing unit 21, as simple graphics at all the capturing positions P on the container map M displayed on the display unit 5, as shown in FIG. 4. For the capturing positions P where there are colonies, for example, for the capturing positions P4, P6, P7, and P8, the control unit 17 surrounds the outer peripheries of the colonies C with lines and displays them at the capturing positions P4, P6, P7, and P8 on the container map M.

For the capturing positions P6 and P7, for example, where there are colonies C that partially protrude from the capturing regions, the control unit 17 calculates estimate values for the protruding regions of the colonies C and also displays, on the container map M, the outer peripheries of the protruding regions of the colonies C beyond the regions of the respective capturing positions P6 and P7. For the capturing position P6 specified on the container map M by the user, for example, the control unit 17 displays, in an enlarged manner, an actual image of the cells S captured at the capturing position P6.

As described above, according to the analysis-result browsing device 1 of this embodiment, the control unit 17 simultaneously displays the analysis results of the cells S (or, colonies C) at all the capturing positions P on the container map M, thereby making it possible for the user to compare the analysis results of the cells S (or, colonies C) at the respective capturing positions P, without switching the analysis results of the cells S (or, colonies C) to be displayed, among the plurality of capturing positions P in the container 9. Therefore, it is possible to grasp, at a glance, how many cells S (or, colonies C) exist at which positions in the container 9.

The protruding regions of colonies C that partially protrude from the capturing positions P are estimated and are also displayed on the container map M, thereby making it possible for the user to grasp, at a glance, the approximate external shapes of the colonies C that are not entirely contained in the corresponding capturing positions P.

In this embodiment, although the analysis results of the cells S are simultaneously displayed at all the capturing positions P on the container map M, the analysis results of the cells S need to be simultaneously displayed merely at at least a plurality of capturing positions P, and, for example, a plurality of capturing positions P at which the analysis results are simultaneously displayed may be selectable.

In this embodiment, although the processing unit 21 detects cells S that are equal to or larger than the predetermined size, instead of this, the processing unit 21 may detect cells S that have brightnesses equal to or larger than a predetermined brightness, for example.

In this embodiment, the control unit 17 may display, in different colors in a contrasting manner on the container map M, cells S that have different shapes, such as differentiated cells S and undifferentiated cells S, or actually captured shapes of cells S and estimated shapes of cells S.

By doing so, the user can easily distinguish between them on the container map M by the difference in color.

In this embodiment, the control unit 17 may calculate, for the respective capturing positions P, feature quantities of colonies C, into which a plurality of cells S are aggregated, on the basis of the analysis results of the cells S analyzed by the processing unit 21 and may display, on the container map M, the calculated feature quantities of the colonies C in association with the corresponding capturing positions P.

The feature quantity can be, for example, the percentage area of the sum of the areas of the colonies C in the capturing region of the capturing position P, the number of colonies C existing in the capturing region of the capturing position P, or the like. By doing so, the user can also grasp the feature of the colonies C for each of the capturing positions P, on the container map M displayed on the display unit 5.

In this embodiment, although the protruding region of a colony C that partially protrudes from the capturing region is estimated and displayed, the protruding region may not be displayed.

In this embodiment, at each of the capturing positions P on the container map M, the external appearances of cells S (or, colonies C) existing at the capturing position P are displayed as simple graphics, as the analysis results of the cells S; however, the analysis-result display method can be modified as follows.

Figure 5:
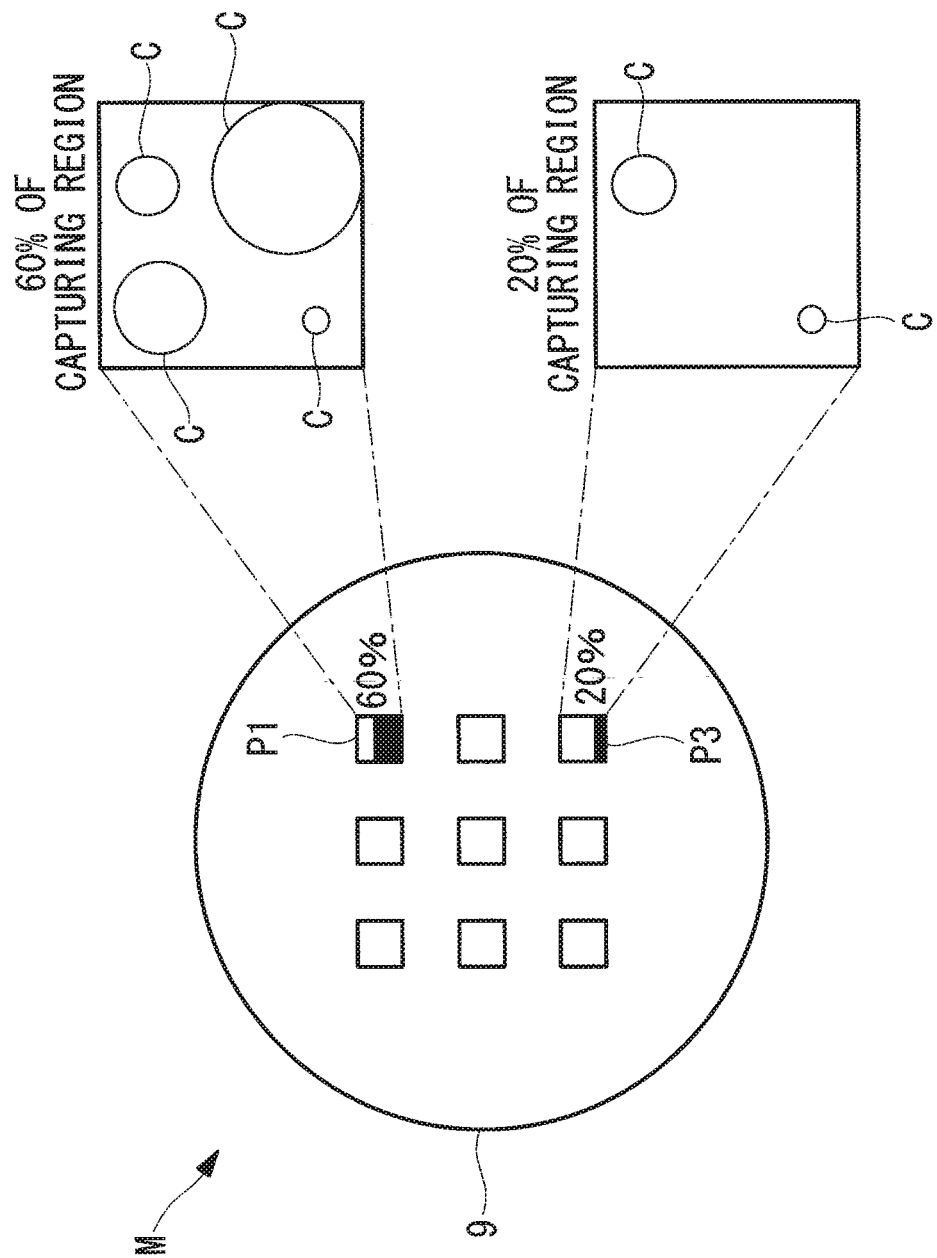
FIG. 5 is a plan view showing a state in which the feature quantities of colonies existing at the respective capturing positions are displayed in histograms, as a modification of analysis results displayed at the respective capturing positions on the container map.

In a first modification, for example, as shown in FIG. 5, at the respective capturing positions P on the container map M, the feature quantities of colonies C (or, cells S) existing at the respective capturing positions P may be displayed in histograms. In the example shown in FIG. 5, the percentage area of the sum of the areas of colonies C in the capturing region of the capturing position P is shown as the feature quantity. By doing so, the distribution of colonies C in the container 9 can be grasped from the graphs of the respective capturing positions P.

In this case, the percentage area of the sum of the areas of colonies C in each of the respective capturing positions P may also be displayed numerically in the vicinity of the capturing position P. In the example shown in FIG. 5, from the histograms and the numerical values, it can be recognized, at a glance, that colonies C exist at the capturing position P1 at 60% of the capturing region thereof, and colonies C exist at the capturing position P3 at 20% of the capturing region thereof. In the example shown in FIG. 5, the capturing positions P1 and P3 are specified by the user, and ROI information indicating the outer peripheries of the colonies C at the capturing positions P1 and P3 is displayed in an enlarged manner.

Figure 6:
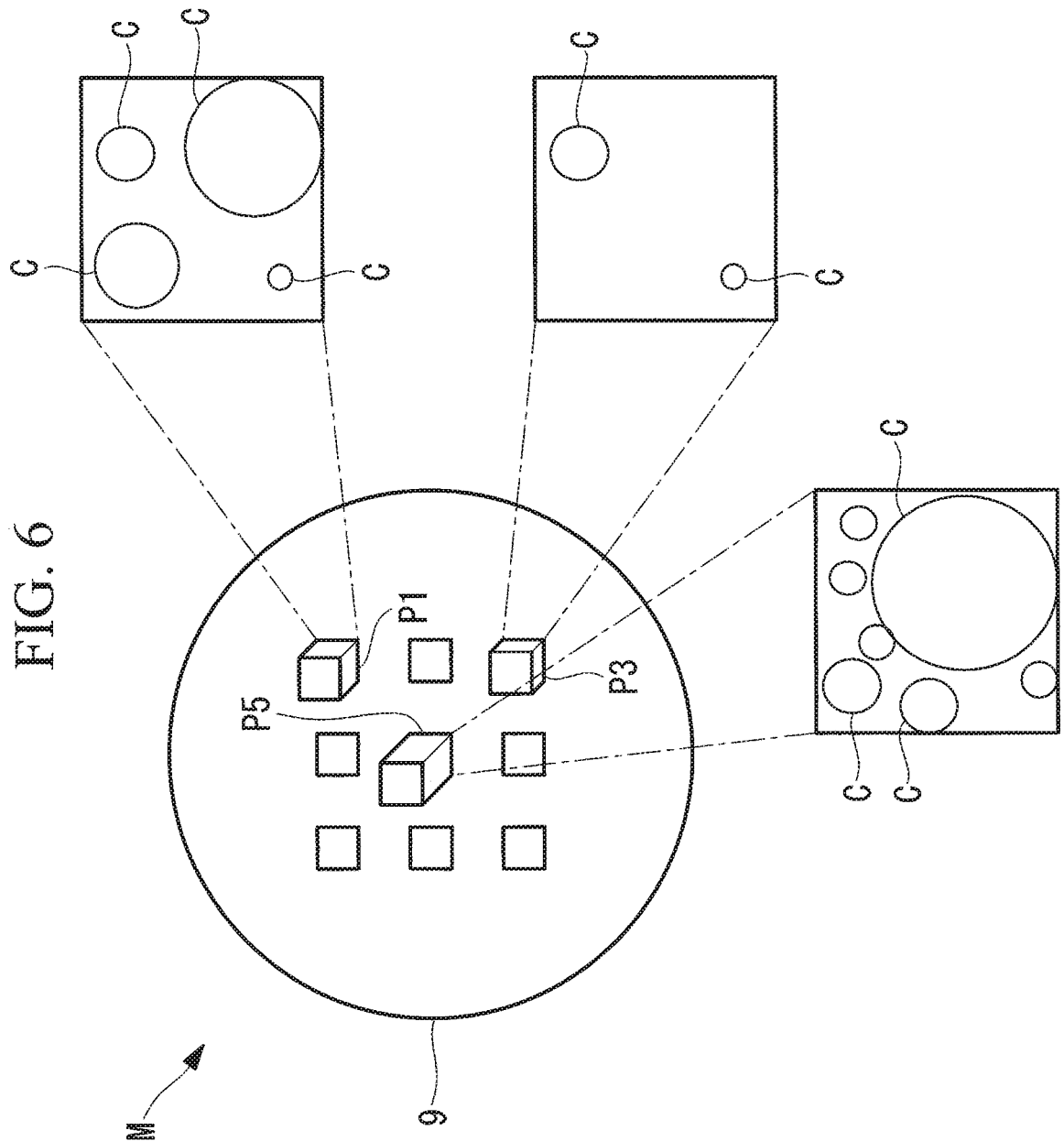
FIG. 6 is a plan view showing a state in which the feature quantities of colonies existing at the respective capturing positions are displayed as 3D shapes, as a modification of analysis results displayed at the respective capturing positions on the container map.

In a second modification, for example, as shown in FIG. 6, at the respective capturing positions P on the container map M, the feature quantities of colonies C (or, cells S) existing at the capturing positions P may be displayed as 3D graphics. In the example shown in FIG. 6, the percentage area of the sum of the areas of colonies C in the region of the capturing position P is shown as the feature quantity. In this case, for example, the height of the 3D graphic may be increased as the percentage area of the colonies C increases. For example, the height of the 3D graphic may be increased as the number of cells S increases or as the area of cells S increases.

By doing so, the distribution of colonies C in the container 9 can be recognized, at a glance, merely by comparing the heights of the 3D graphics at the respective capturing positions P. In the example shown in FIG. 6, the capturing positions P1, P3, and P5 are specified by the user, and ROI information indicating the outer peripheries of colonies C in the capturing positions P1, P3, and P5 is displayed in an enlarged manner.

In a third modification, for example, as shown in FIG. 7, at the respective capturing positions P on the container map M, the feature quantities of colonies C (or, cells S) existing at the capturing positions P may be displayed in color gradation. In the example shown in FIG. 7, the percentage area of the sum of the areas of colonies C in the region of the capturing position P is shown as the feature quantity. In this case, for example, the color of the capturing position P may be deepened as the percentage area of the colonies C increases. For example, the color of the capturing position P may be deepened as the number of cells S increases or as the area of the cells S increases.

By doing so, the distribution of colonies C (or, cells S) in the container 9 can be grasped, at a glance, merely by comparing the color gradations. In the example shown in FIG. 7, the capturing positions P1 and P3 are specified by the user, and ROI information indicating the outer peripheries of colonies C at the capturing positions P1 and P3 is displayed in an enlarged manner.

In the above-described variations of the display methods shown in FIGS. 4 to 7, the content to be displayed at each of the capturing positions P on the container map M may be switched according to the capturing time, for example, as shown in FIG. 8, on the basis of the analysis results of cells S (or, colonies C) at the corresponding capturing position P that are obtained through time-lapse capturing and that are accumulated by the recording unit 19 of the PC 7.

By doing so, the user can confirm changes in the states of cells S (or, colonies C) at capturing-time intervals, as in a moving image. FIG. 8 shows a state in which changes in the shapes of colonies C from the start of capturing on a daily basis is displayed at each of the capturing positions P on the container map M.

In this embodiment, at each of the capturing positions P on the container map M, a change in the proliferation rate of cells S may be displayed in a histogram on a time-lapse basis.

In this embodiment and the above-described first to third modifications, for example, as shown in FIG. 9, the control unit 17 may estimate a feature quantity of cells S (or, colonies C) that exist in a region, other than the capturing positions P, on the container map M on the basis of the analysis results of cells S (or, colonies C) analyzed by the processing unit 21 and may display the estimated feature quantity of the cells S (or, colonies C) on the container map M.

In the example shown in FIG. 9, in a region located between the capturing position P1 and the capturing position P2, the estimated percentage area of the sum of the areas of colonies C in this region is displayed in gradation.

By doing so, the user can grasp approximate features of colonies C that exist in the container 9 and that are not captured by the camera 13, the colonies C being aggregates of cells S.

As a result, the following aspects are derived from the above-described embodiment.

According to one aspect, the present invention provides an analysis-result browsing device including: a capturing-position setting unit that sets capturing positions in a container that contains cells; an image acquisition unit that captures the cells that exist at the capturing positions set by the capturing-position setting unit; an analysis unit that detects and analyzes, for the respective capturing positions, the cells captured by the image acquisition unit; a display unit that displays analysis results of the cells analyzed by the analysis unit, together with a container map that shows the container and the plurality of capturing positions in the container; and a display control unit that simultaneously displays the analysis results of the cells at at least two of the capturing positions on the container map, which is displayed on the display unit.

According to this aspect, cells are captured by the image acquisition unit at the capturing positions in the container, which are set by the capturing-position setting unit, and the captured cells are detected and analyzed by the analysis unit. Analysis results of the cells for the respective capturing positions analyzed by the analysis unit are displayed on the display unit, together with the container map, which shows the container and the plurality of capturing positions in the container.

In this case, the analysis results of the cells are simultaneously displayed, by the display control unit, at at least two of the capturing positions on the container map, thereby making it possible for the user to grasp, at a glance, how many cells exist at which positions in the container, without the need of switching the analysis results of the cells to be displayed, between the at least two of the capturing positions in the container.

In the above-described aspect, the display control unit may display, at the capturing positions on the container map in a distinguishable manner, the outer periphery of a colony into which two or more of the cells detected by the analysis unit are aggregated.

With this configuration, the user can visually and easily grasp, at the capturing positions on the container map, which is displayed on the display unit, the shapes and the sizes of colonies that exist at the capturing positions.

In the above-described aspect, when the colony has a protruding region that partially protrudes from the corresponding capturing position, the display control unit may estimate the protruding region of the colony on the basis of the analysis results of the cells analyzed by the analysis unit and may display the estimated protruding region on the container map.

With this configuration, the user can grasp, at a glance, approximate external shapes of colonies that do not entirely fit within the capturing positions on the container map.

In the above-described aspect, the display control unit may calculate the feature quantity of a colony into which two or more of the cells are aggregated, on the basis of the analysis results of the cells analyzed by the analysis unit and may display the calculated feature quantity on the container map in association with the corresponding capturing position.

With this configuration, the user can also grasp the feature of a colony for each of the capturing positions on the container map, which is displayed on the display unit.

In the above-described aspect, the display control unit may display the feature quantities as 3D graphics, graphs, or color gradations, in a comparable manner at at least two of the capturing positions on the container map.

With this configuration, the feature quantities of colonies can be visually and easily compared between the at least two of the capturing positions.

In the above-described aspect, the display control unit may estimate the feature quantity of a colony that exists in a region, other than the capturing positions, on the container map on the basis of the analysis results of the cells analyzed by the analysis unit and may display the estimated feature quantity of the colony on the container map.

With this configuration, the user can also grasp an approximate feature of a colony, which is an aggregate of cells, that exists in the container and that is not captured by the image acquisition unit.

REFERENCE SIGNS LIST 1 analysis-result browsing device
5 display unit
13 camera (image acquisition unit)
17 control unit (capturing-position setting unit, display control unit)
21 processing unit (analysis unit)
S cells

The invention claimed is:

1. An analysis-result browsing device comprising:
a computer;
a camera; and
a display,
wherein the computer is configured to execute processes comprising:
   a capturing-position setting process to set capturing positions in a container that contains cells;
   an image acquisition process to control the camera to capture images of cells that exist at the capturing positions set in the capturing-position setting process;
   an analysis process to detect and analyze, for the respective capturing positions, the cells based on the images captured in the image acquisition process; and
   a display control process to control the display to display analysis results of the cells analyzed in the analysis process, together with a container map that shows the container and the plurality of capturing positions in the container, and
wherein the display control process comprises simultaneously displaying in a distinguishable manner, at areas corresponding to at least two of the capturing positions on the container map displayed on the display at which at least two of the cells are aggregated, information regarding the analysis results of the cells that exist at the at least two of the capturing positions.

2. The analysis-result browsing device according to claim 1, wherein the display control process comprises displaying, at a corresponding one of the capturing positions on the container map in a distinguishable manner, an outer periphery of a colony into which at least two of the cells detected in the analysis process are aggregated.

3. The analysis-result browsing device according to claim 2, wherein the display control process comprises, when the colony has a protruding region that partially protrudes from its corresponding capturing position, estimating the protruding region of the colony based on the analysis results of the cells analyzed in the analysis process, and displaying the estimated protruding region on the container map.

4. The analysis-result browsing device according to claim 1, wherein the display control process comprises calculating a feature quantity of a colony into which at least two of the cells are aggregated, based on the analysis results of the cells analyzed in the analysis process, and displaying the calculated feature quantity on the container map in association with the capturing position to which the colony corresponds.

5. The analysis-result browsing device according to claim 4, wherein the display control process displays the feature quantities as 3D graphics, graphs, or color gradations, in a comparable manner at at least two of the capturing positions on the container map.

6. The analysis-result browsing device according to claim 4, wherein the display control process comprises estimating the feature quantity of a colony that exists in a region, other than the capturing positions, on the container map based on the analysis results of the cells analyzed in the analysis process, and displaying the estimated feature quantity of the colony on the container map.

* * * * *